(12) United States Patent
Mintz et al.

(10) Patent No.: US 12,059,158 B2
(45) Date of Patent: Aug. 13, 2024

(54) EXPANDABLE-MOUTH CATHETER DELIVERY-ASSIST TOOL

(71) Applicant: Covidien LP, Mansfield, MA (US)

(72) Inventors: Eric Mintz, Newport Beach, CA (US); Ujwal Jalgaonkar, Irvine, CA (US); Syamala Rani Pulugurtha, Irvine, CA (US); Bin Wang, Irvine, CA (US); Christoph A. Efstathiou, San Diego, CA (US)

(73) Assignee: Covidien LP, Mansfield, MA (US)

(*) Notice: Subject to any disclaimer, the term of this patent is extended or adjusted under 35 U.S.C. 154(b) by 193 days.

(21) Appl. No.: 17/391,556

(22) Filed: Aug. 2, 2021

(65) Prior Publication Data
US 2023/0030799 A1 Feb. 2, 2023

(51) Int. Cl.
*A61B 17/12* (2006.01)
*A61M 39/06* (2006.01)
*A61B 17/00* (2006.01)

(52) U.S. Cl.
CPC .... *A61B 17/1215* (2013.01); *A61B 17/12109* (2013.01); *A61M 39/06* (2013.01); *A61B 2017/00871* (2013.01); *A61B 2017/1205* (2013.01)

(58) Field of Classification Search
CPC ......... A61B 17/1215; A61B 17/12109; A61M 39/06
See application file for complete search history.

(56) References Cited

U.S. PATENT DOCUMENTS

| | | | |
|---|---|---|---|
| 2001/0044595 A1* | 11/2001 | Reydel | A61M 25/0668 604/523 |
| 2003/0176910 A1* | 9/2003 | Vrba | A61F 2/95 623/1.11 |
| 2006/0041302 A1* | 2/2006 | Malewicz | A61F 2/966 623/1.11 |

(Continued)

FOREIGN PATENT DOCUMENTS

WO 2021113962 A1 6/2021

OTHER PUBLICATIONS

U.S. Appl. No. 17/111,266, naming inventors Mintz et al., filed Dec. 3, 2020, and entitled, "Catheter Including a Radiopaque Expandable Member".

*Primary Examiner* — Thomas McEvoy
(74) *Attorney, Agent, or Firm* — Shumaker & Sieffert, P.A

(57) ABSTRACT

In some examples, a medical assembly includes a catheter and a delivery-assist tool. The catheter includes an elongated body comprising a proximal body portion and a distal body portion and defining a body inner lumen; and an expandable member located at the distal body portion, the expandable member defining an expandable member inner lumen. The delivery-assist tool includes a support structure configured to extend through the body inner lumen and the expandable member inner lumen of the catheter; and a flexible cover coupled to a distal portion of the support structure, wherein the flexible cover is configured to facilitate compression and retention of the expandable member in a delivery configuration while being advanced through a delivery sheath and while the support structure extends through the body inner lumen and the expandable member inner lumen.

25 Claims, 6 Drawing Sheets

(56) References Cited

U.S. PATENT DOCUMENTS

| | | | |
|---|---|---|---|
| 2006/0200221 A1* | 9/2006 | Malewicz | A61F 2/9661 623/1.11 |
| 2007/0276461 A1* | 11/2007 | Andreas | A61F 2/958 623/1.11 |
| 2010/0069852 A1* | 3/2010 | Kelley | A61F 2/95 604/500 |
| 2011/0098804 A1* | 4/2011 | Yeung | A61F 2/2412 623/2.1 |
| 2011/0218613 A1* | 9/2011 | Leopold | A61F 2/95 623/1.2 |
| 2011/0245917 A1* | 10/2011 | Savage | A61F 2/2436 623/2.11 |
| 2013/0197621 A1* | 8/2013 | Ryan | A61M 39/0606 623/1.11 |
| 2013/0204345 A1* | 8/2013 | Cully | A61F 2/966 29/446 |
| 2013/0226276 A1 | 8/2013 | Newell et al. | |
| 2013/0317589 A1 | 11/2013 | Martin et al. | |
| 2014/0371777 A1* | 12/2014 | Rudakov | A61B 17/1214 606/198 |
| 2014/0371778 A1* | 12/2014 | Rudakov | A61B 17/12036 606/198 |
| 2015/0066127 A1 | 3/2015 | Johnson et al. | |
| 2017/0296367 A1* | 10/2017 | Dorn | A61F 2/966 |
| 2018/0368863 A1* | 12/2018 | Skillrud | A61B 17/221 |
| 2019/0269491 A1* | 9/2019 | Jalgaonkar | A61M 25/0067 |
| 2020/0345978 A1* | 11/2020 | Jalgaonkar | A61B 17/1204 |
| 2020/0368514 A1* | 11/2020 | Chalekian | A61M 39/06 |
| 2021/0169494 A1* | 6/2021 | Naglreiter | A61B 17/12109 |

\* cited by examiner

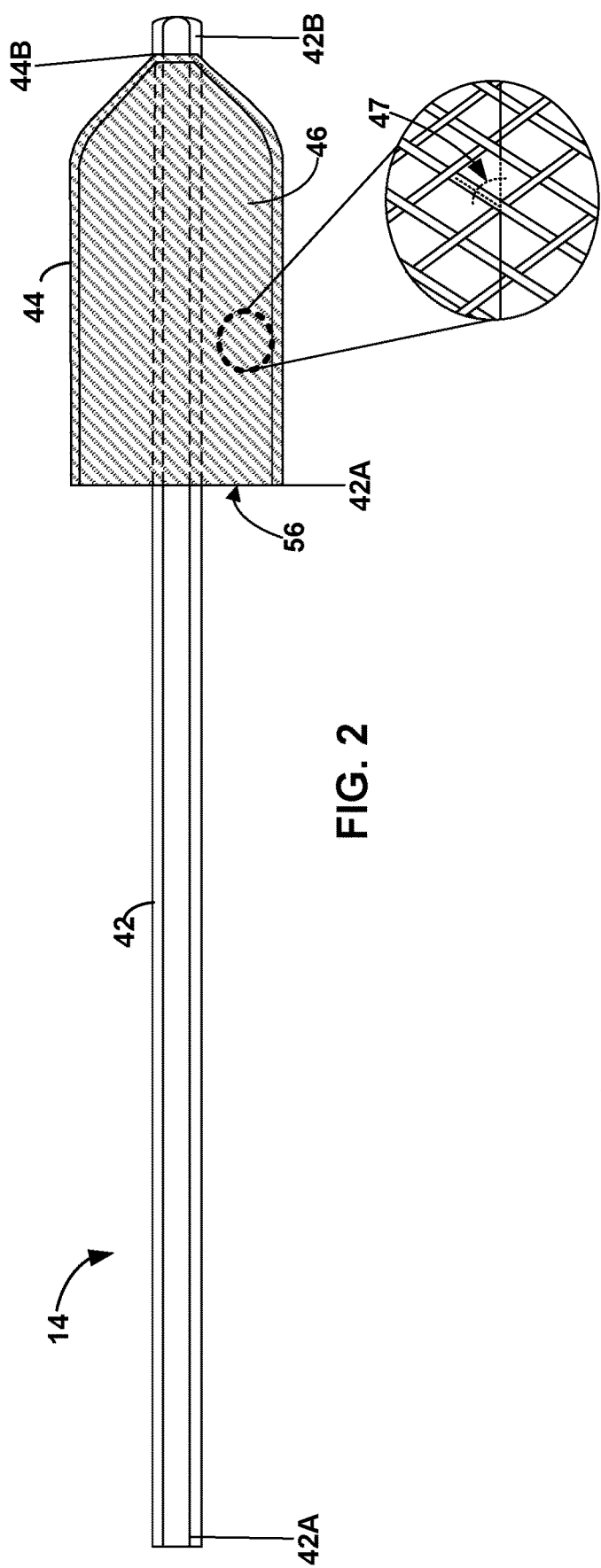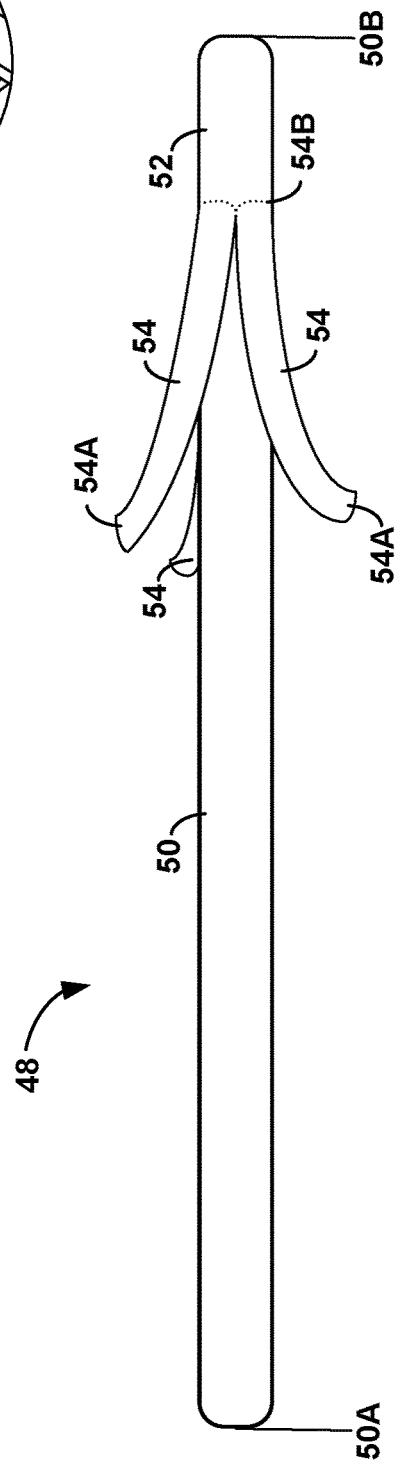

EXPANDABLE-MOUTH CATHETER DELIVERY-ASSIST TOOL

TECHNICAL FIELD

This disclosure relates to a medical assembly including a catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example medical assemblies, including a catheter and a delivery-assist tool. The delivery-assist tool is configured to facilitate delivery of the catheter through a delivery sheath by at least facilitating compression and retention of an expandable member of the catheter while it is being delivered through the delivery sheath. Such constraint of the expandable member may reduce the push force required to deliver the catheter through the sheath relative to examples in which the expandable member is directly introduced and advanced through the delivery sheath without the aid of the delivery-assist tool. The delivery-assist tool includes an elongated support structure configured to be introduced through an inner lumen of the catheter, and a flexible cover configured to cover the expandable member of the catheter to facilitate distal advancement of the catheter through a delivery sheath. For example, as the flexible cover is introduced into a lumen of the delivery sheath, the flexible cover may begin to neck down and cause the expandable member of the catheter to elongate and neck down as well. As a result, the flexible cover may exert an axial tensile force on the expandable member which may minimize the force of delivery (e.g., by avoiding the bunching and compression of the expandable member that may result from a compressive pushing force).

In some examples, the flexile cover includes a flexible mesh configured to apply both an inward radial force (e.g., transmitted to the flexible cover by a delivery sheath) and a proximal axial force onto an outer surface of the expandable member to cause the expandable member to neck down into the delivery configuration. In the delivery configuration, the expandable member defines an outer diameter that is smaller than an inner diameter of the delivery sheath. In this way, the delivery-assist tool reduces an amount of force required to advance the catheter through the delivery sheath, that would otherwise result from friction between the expandable member and the delivery sheath.

Once the expandable member of the catheter is positioned at a target treatment site within vasculature of the patient, the flexible cover may be inverted and proximally withdrawn through the inner lumen of the catheter, thereby enabling expansion of the expandable member to the deployed configuration.

This disclosure also describes examples of methods of using the medical assemblies described herein.

In some examples, a medical assembly includes a catheter including an elongated body that includes a support structure configured to extend through the body inner lumen and the expandable member inner lumen; and a flexible cover coupled to a distal portion of the support structure, wherein the flexible cover is configured to facilitate compression and retention of the expandable member in the delivery configuration while the catheter is being advanced through a delivery sheath and while the support structure extends through the body inner lumen and the expandable member inner lumen.

In some examples, a method includes introducing a delivery tool comprising an elongated support structure and a flexible cover into an inner lumen of a catheter, wherein introducing the delivery tool comprises advancing the elongated support structure and the flexible cover through the inner lumen and positioning the flexible cover distal to an expandable member of the catheter; while the elongated support structure is positioned within the inner lumen of the catheter, positioning the flexible cover over the expandable member of the catheter; distally introducing the catheter and the delivery tool into a delivery sheath, wherein the flexible cover is configured to facilitate compression and retention of the expandable member into a delivery configuration while the expandable member and the flexible cover are advanced through the delivery sheath; and applying a proximal force to the elongated support structure to invert the flexible cover and withdraw the flexible cover into the inner lumen of the catheter, enabling the expandable member to expand.

In some examples, a catheter includes an elongated body including a proximal body portion and a distal body portion and defining a body inner lumen; an expandable member located at the distal body portion, the expandable member forming an expandable member inner lumen, the expandable member inner lumen defining a distal extension of the body inner lumen, wherein the expandable member is configured to expand radially outward from a delivery configuration to a deployed configuration; and a delivery-assist tool configured to be received within the body inner lumen and the expandable member inner lumen, the delivery-assist tool comprising a support structure and a mesh cover configured to apply an axial tensile force to the expandable member to facilitate compression of the expandable member into the delivery configuration as the expandable member and the mesh cover are advanced through a delivery sheath.

In some examples, a method includes advancing a catheter assembly through an outer sheath, wherein the assembly comprises: an elongated body comprising a proximal body portion and a distal body portion and defining a body inner lumen; an expandable member located at the distal body portion, the expandable member defining an expandable member inner lumen, wherein the expandable member is configured to expand radially outward from a delivery configuration to a deployed configuration; a support structure configured to extend through the body inner lumen and the expandable member inner lumen; and a flexible cover coupled to a distal portion of the support structure, wherein the flexible cover is configured cover the expandable member, wherein as the catheter assembly is advanced through the outer sheath, the flexible cover applies an axial tensile force to the expandable member to facilitate advancement of the expandable member through the outer sheath.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 2 is a side view of a distal portion of an example of the delivery-assist tool of the assembly of FIGS. 1A and 1B.

FIG. 3 is side view of a distal portion of another example of the delivery-assist tool of the assembly of FIGS. 1A and 1B.

DETAILED DESCRIPTION

Figure 1A:
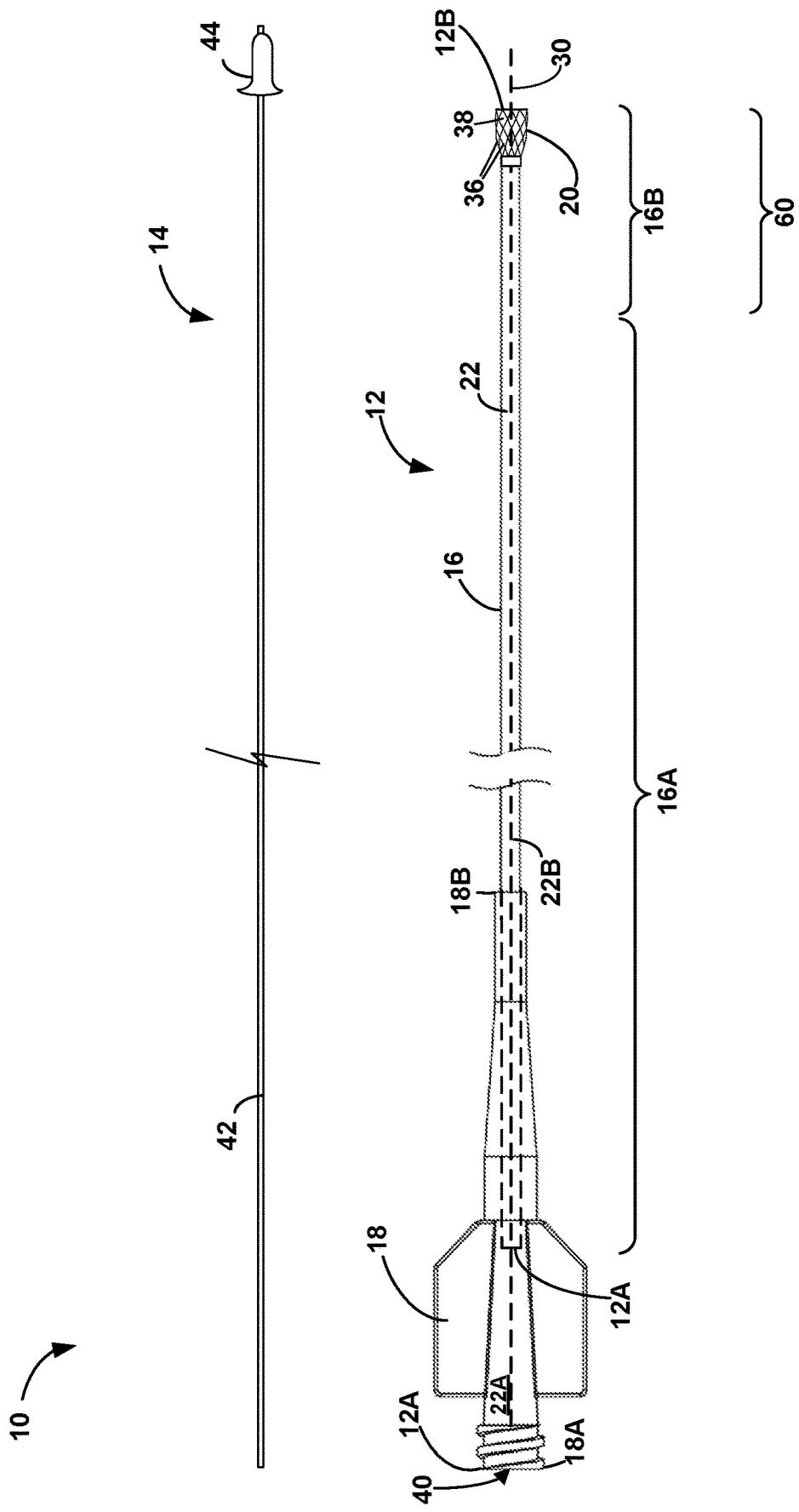
FIG. 1A is a conceptual side view of an example medical assembly, which includes a catheter and a delivery-assist tool for the catheter.

The disclosure describes a medical assembly including an expandable-mouth catheter and a delivery-assist tool configured to facilitate delivery of the catheter through a delivery sheath by at least constraining an expandable member of the catheter while it is being delivered through the delivery sheath.

Example catheters described herein include a relatively flexible elongated body configured to be navigated through vasculature of a patient, e.g., tortuous vasculature in a brain of the patient. A distal portion (e.g., a distal tip) of the catheter includes an expandable member, such as an expandable stent-like structure or an expandable braid or other mesh-like structure, positioned at a distal portion of the elongated body. The expandable member is configured to expand radially outward within a hollow anatomical structure (e.g., a blood vessel) of the patient. This may enable, for example, the expandable member to engage with a thrombus, such as a clot, embolism, or other material such as plaques or foreign bodies, during an aspiration procedure, such as, but not limited to, a medical procedure using A Direct Aspiration first-Pass Technique (ADAPT) for acute stroke thrombectomy.

The expandable member may help improve aspiration of the thrombus into the catheter by providing a relatively large luminal diameter (and therefore exert a larger aspiration force against the thrombus or other material to be removed) and interior space for the thrombus to engage with the catheter compared to examples in which an otherwise similar catheter does not include an expandable member. In contrast, a catheter that does not include an expandable member may have more limited radial expansion and may thus make it harder to aspirate a thrombus (e.g., due to a smaller cross-sectional dimension of the distal end of the catheter). The expandable member may overcome such radial expansion limitations, thereby increasing thrombus engagement, reducing the amount of time required for revascularization, and increasing revascularization success rates for various procedures, as compared to similar procedures performed using catheters that do not include an expandable member to engage a thrombus.

Some expandable-mouth catheters may be limited in their potential use, e.g., with respect to the amount that the expandable member is able to expand, due to the relative difficulty of delivering larger-diameter catheters through a delivery sheath, e.g., an outer guide catheter or an introducer sheath. For instance, while the expandable member is advanced through the delivery sheath, the expandable member may impart an outward radial force onto an interior surface of the sheath, which in some cases, may result in a significant frictional counterforce that impedes advancement through the sheath. Additionally, or alternatively, in some cases, the relatively soft, flexible distal portion (e.g., the expandable member) of the catheter may tend to longitudinally deform or "bunch up" in response to a distal pushing force applied to the elongated body of the catheter and/or friction from the interior surface of the delivery sheath.

According to examples of this disclosure, the delivery-assist tool includes a flexible cover configured to facilitate compression of the expandable member of the catheter into a delivery configuration and facilitate retention of the expandable member in a configuration that facilitates distal advancement of the expandable member through a delivery sheath. The flexible cover is positioned on a distal portion of an elongated support structure, which is configured to be introduced through an inner lumen of the catheter. The flexible cover is configured to receive the expandable member of the catheter and redirect a compression force from an interior surface of the delivery sheath to neck down the expandable member to facilitate insertion of the catheter into the delivery sheath and facilitate distal advancement of the catheter through the delivery sheath.

Such constraint of the expandable member may reduce the pushing force required to advance the catheter through the delivery sheath, as compared to examples in which the expandable member is directly introduced into, and advanced through, the delivery sheath without the aid of such a delivery-assist tool. For example, as the flexible cover is introduced into a lumen of the delivery sheath, the flexible cover may begin to contract radially (or "neck down") due to the compressive force applied by the inner surface of the delivery sheath, and the necking down of the flexible cover may cause the expandable member of the catheter to elongate and neck down as well. As a result, the flexible cover may exert a tensile pulling force on the expandable member which may reduce the force of delivery (e.g., by avoiding the bunching and compression of the expandable member that may result from a longitudinally compressive pushing force).

In some examples, the flexible cover includes a flexible mesh configured to apply both an inward radial force and a proximal axial force onto an outer surface of the expandable member to cause the expandable member to neck down into the delivery configuration. The inward radial force can be, for example, applied to the flexible mesh by the inner surface of the delivery sheath. In the delivery configuration, the flexible cover (containing the expandable member) defines an outer diameter that is smaller than an inner diameter of the delivery sheath. In this way, the delivery-assist tool reduces an amount of force required to introduce the catheter through the delivery sheath, that would otherwise result from friction between the expandable member and the sheath.

Once the expandable member of the catheter is positioned at a target treatment site within vasculature of the patient, the flexible cover may be inverted and proximally withdrawn through the inner lumen of the catheter, thereby enabling expansion of the expandable member to the deployed configuration.

Figure 1B:
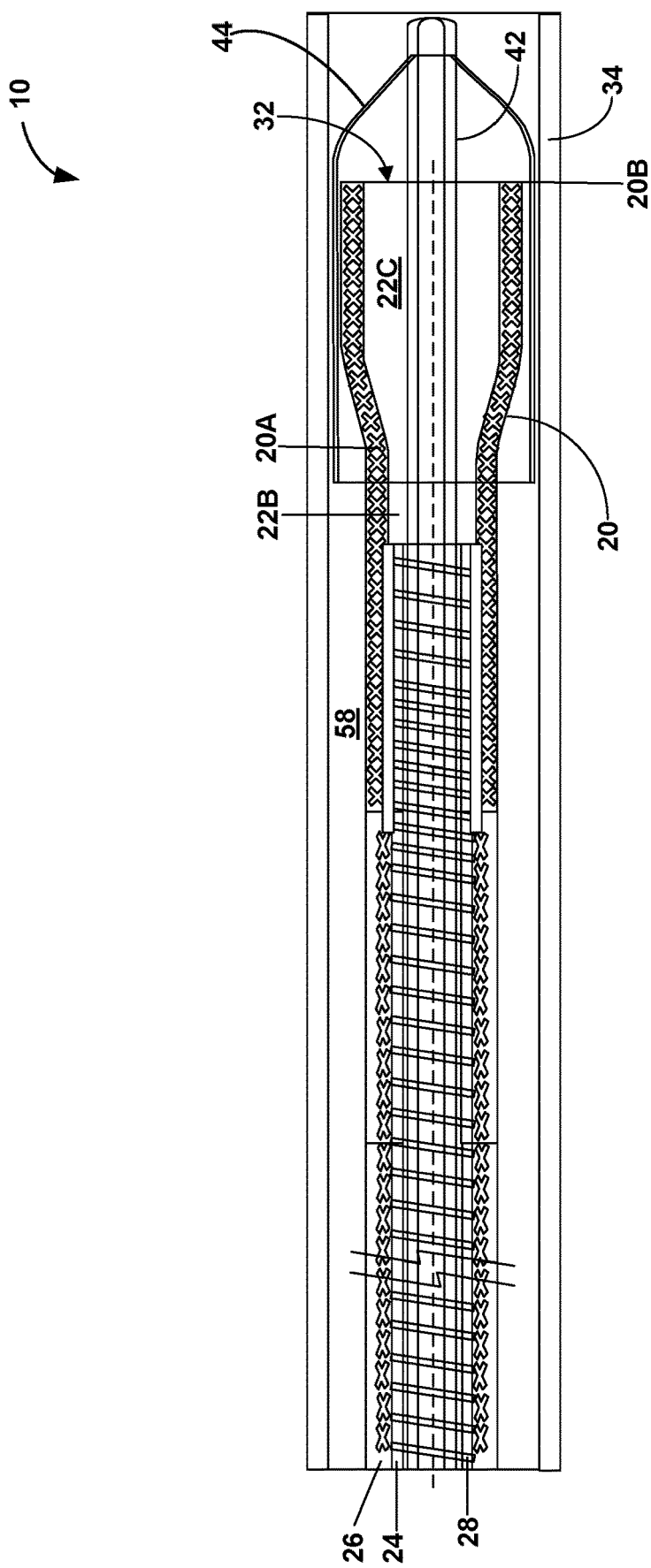
FIG. 1B is a conceptual cross-sectional view of a distal portion of the medical assembly of FIG. 1A, showing a flexible cover of the delivery-assist tool positioned over an expandable member of the catheter and inserted within a delivery sheath, wherein the cross-section is taken through a center of the catheter and along a longitudinal axis.

FIG. 1A is a side view, and FIG. 1B is a conceptual cross-sectional view, of an example medical assembly 10 that includes at least an expandable-mouth catheter 12 and a delivery-assist tool 14 for catheter 12. As shown in FIG. 1A, catheter 12 can include an elongated body 16, a hub 18, and an expandable member 20. Catheter 12 defines an inner lumen 22, which may include a hub lumen 22A, a body lumen 22B, and/or an expandable member lumen 22C.

Elongated body 16 is configured to be advanced through vasculature of a patient via a pushing force applied to proximal body portion 16A (e.g., via hub 18) of elongated body 16 without buckling, kinking, or otherwise undesirably deforming (e.g., ovalization). As shown in FIG. 1B, elongated body 16 can include a plurality of concentric layers, such as an inner liner 24, an outer jacket 26, and a structural support member 28 positioned between at least a portion of inner liner 24 and at least a portion of outer jacket 26. Elongated body 16 includes a proximal body portion 16A and a distal body portion 16B, which are each longitudinal sections of elongated body 16 and do not overlap in the longitudinal direction (along longitudinal axis 30). Elongated body 16 defines at least one body lumen 22B (also referred to as a body inner lumen). In the example shown in FIG. 1A, a proximal end of elongated body 16 is received within hub 18 and is mechanically connected to hub 18 via an adhesive, welding, or another suitable technique or combination of techniques. Inner lumen 22 of catheter 12 may be defined by portions of hub 18, inner liner 24, and expandable member 20.

Catheter 12 may be used as an aspiration catheter to remove a thrombus or other material from vasculature of a patient. A suction force (e.g., a vacuum) may be applied to proximal end 12A of catheter 12 (e.g., via hub 18) to draw a thrombus or other blockage into inner lumen 22. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 12 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 16 may be structurally configured to be relatively flexible, pushable, and relatively kink- and buckle-resistant, so that it may resist buckling when a pushing force is applied to a relatively proximal section of catheter 12 (e.g., via hub 18) to advance elongated body 16 distally through vasculature, and so that it may resist kinking when traversing around a tight turn in the vasculature. In some examples, elongated body 16 is configured to substantially conform to the curvature of the vasculature. In addition, in some examples, elongated body 16 has a column strength and flexibility that allow at least distal body portion 16B of elongated body 16 to be navigated from a femoral artery, through the aorta of the patient, and into the intracranial vascular system of the patient, e.g., to reach a relatively distal treatment site. Alternatively, elongated body 16 can have a column strength (and/or be otherwise configured) to enable the distal portion 16B to be navigated from a radial artery via an access site in the arm, e.g., at or near the wrist, through the aorta of the patient or otherwise to a common carotid or vertebral artery, and into the intracranial vascular system of the patient, e.g., to reach a relatively distal treatment site.

Although primarily described as being used to reach relatively distal vasculature sites, catheter 12 may also be configured to be used with other target tissue sites. For example, catheter 12 may be used to access tissue sites throughout the coronary and peripheral vasculature, the gastrointestinal tract, the urethra, ureters, fallopian tubes, veins, and other hollow anatomical structures of a patient.

Expandable member 20 is configured to radially expand (e.g. self-expand) within a vessel of a patient, e.g., to engage a thrombus within the vessel. Expandable member 20 is positioned at distal body portion 16B of elongated body 16, such that a distal end of expandable member 20 defines distal end 12B of catheter 12 and a distal mouth 32 open to inner lumen 22 of catheter 12. For example, expandable member lumen 22C (also referred to as an expandable member inner lumen) forms a distal extension of the inner lumen 22B of the elongated body 16. In these examples, expandable member lumen 22C is in fluid communication with inner lumen 22B of elongated body 16.

Expandable member 20 can include a frame configured to expand radially outward from a compressed or delivery configuration to an expanded or deployed configuration, thereby expanding lumen 22C radially outward. For example, the expandable frame can enable expandable member 20 to maintain its expanded shape (after it is expanded), even in the presence of a suction force applied to inner lumen 22 of catheter 12 during an aspiration process. Example expandable frames include an expandable stent-like structure or an expandable tubular braid, weave, laser-cut mesh, or other mesh-like configuration, which can each be formed from a plurality of structural elements. For example, each structural element can comprise a wire or filament. In some examples, expandable member 20 may resemble a braided structure or mesh-like structure that includes a tubular body comprising a plurality of filaments 36, which can be braided or interwoven to form the frame, or members of a laser-cut frame. Filaments 36 may be forced apart and radially outward from one another to increase the diameter at various portions of expandable member 20.

In any of these examples, expandable member 20 may include a flexible membrane 38 coupled to (e.g., radially inward and/or radially outward of) the expandable frame or integrated into the expandable frame. In some examples, flexible membrane 38 may be formed of an elastomeric material, such as polyolefin thermoplastic elastomers, polyurethane elastomeric alloys, or silicone, that permits the expansion of expandable member 20. Membrane 38 can act as a fluid barrier in some examples. In other examples, expandable member 20 does not include such flexible membrane 38.

Expandable member 20 is configured to collapse into a delivery configuration for delivery into vasculature of a patient, e.g., through a delivery sheath 34 and expand radially outward within a blood vessel of a patient. This increased radial flexibility (e.g., range of expandability in a radial direction) may be useful, for example, when a relatively smaller delivery sheath is required for insertion via certain vasculature access sites, such as the radial artery. As one non-limiting example, a radial-access sheath may have an inner diameter of about 5 French, as compared to about 6 French for femoral-access sheaths. Accordingly, a smaller diameter (or other maximum cross-sectional dimension) catheter 12 may be useful for such applications.

In some examples, in its expanded states, expandable member 20 defines a tubular, cylindrical, or funnel shape configured to provide catheter 12 with a relatively large diameter (or other maximum cross-sectional diameter) distal end 12B (compared to, for example, proximal body portion 16A of elongated body 16) and interior space 22C for better engagement with a thrombus (e.g., clot or embolus). In some examples, the cross-section of expandable member 20 in its expanded state may be round (e.g., circular) and the cross-sectional axis may be referred to as a diameter. In some examples, the cross-section may be irregularly shaped, in which case the cross-sectional dimension may be referred to as the major axis (e.g., a longest dimension of the cross-section). In the expanded configuration, the cross-section of expandable member 20 may be wider at a distal end than a proximal end. For example, in the expanded configuration, the inner diameter at the distal end of expandable member 20 (e.g., at or near distal opening 32) may be about 150 percent to about 300 percent wider than an inner diameter of expandable member 20 near proximal end 20A of expandable member 20.

Expandable member 20 can be configured to facilitate thrombus removal. In examples in which catheter 12 is used with an aspiration procedure (e.g., ADAPT technique), the size and shape of expandable member 20 may enable catheter 12 to better engage a thrombus by increasing the distal opening 32 into which the thrombus may be received, increasing the total aspiration force exerted on the thrombus via a larger luminal area, and/or by distributing the aspiration forces over a greater portion of the thrombus rather than a localized area, thereby allowing the thrombus to be aspirated into catheter 12 more effectively. Expandable member 20 enables catheter 12 to maintain a relatively small-diameter elongated body 16 (e.g., within proximal body portion 16A) to facilitate navigability of catheter 12, while also enabling catheter 12 to exhibit improved engagement and suction force characteristics that may be attributed to having a large-diameter distal end 12B. In some examples, the presence of expandable member 20 may lead to improved revascularization success rates, such as due to the improved thrombus engagement and/or suction (e.g., to better pull the entirety of the thrombus into catheter 12 during aspiration) as described herein.

In addition, expandable member 20 can be configured to exhibit a relatively low longitudinally compressive stiffness, which can facilitate thrombus removal. For example, when combined with cyclical aspiration, in which suction force applied to inner lumen 22 of catheter 12 is varied over time, the relatively low longitudinally compressive stiffness of expandable member 20 may enable the expandable member 20 to undergo "flutter"-type motion, in which expandable member 20 alternatingly contracts and expands in an axial direction (e.g., parallel to longitudinal axis 30), e.g., at a periodic frequency. This cyclical longitudinal contraction and expansion of expandable member 20 can in turn cause cyclical axial motion of the distal mouth 32 relative to the (stationary or relatively stationary) thrombus, which may facilitate dislodgment of the thrombus from vasculature. Additionally, as the expandable member 20 contracts longitudinally rather than radially in response to the application of cyclical aspiration, distal mouth 32 of expandable member 20 may remain more open and engaged with the thrombus, thereby further facilitating removal of the thrombus.

Expandable member 20 may be of any suitable length and diameter, which may be selected based on the target vessel or particular procedure being performed. For example, expandable member 20 may be made be long enough to fully engulf a thrombus (e.g., an average amount of thrombus material). In some examples, expandable member 20 may be about 2 centimeters to about 25 centimeters long, measured in a direction parallel to longitudinal axis 30. For example, expandable member 20 may be about 1.5 cm, about 2.0 cm, or about 25 cm in length, such as from about 0.5 cm to about 3.0 cm.

As discussed above, in some examples, in the delivery configuration, a distal section of expandable member 20 may have a cross-sectional dimension substantially equal to (e.g., equal to or nearly equal to) or only marginally greater than the outer diameter of elongated body 16 proximate to expandable member 20. In some examples in which expandable member 20 defines a tube shape or a cylinder shape (having an open distal mouth 32) in an expanded (deployed) state, expandable member 20 may define a substantially constant diameter (e.g., constant, or nearly constant in the absence of forces compressing expandable member 20) along about 0.5 cm to about 3 cm, or 0.5 cm to about 2.5 cm of a length of expandable member 20, which can be a distal-most length in some examples.

In some examples, the expandability of expandable member 20 may enable the cross-sectional dimension of elongated body 16 within proximal body portion 16A to remain comparatively small. As described above, such a combination may enable catheter 12 to exhibit the improved navigability characteristics of a catheter body with a small diameter while still providing catheter 12 with the improved engagement and suction characteristics that may be attributed to having a large-diameter distal end 12B.

In some examples, an inner surface of expandable member 20 may comprise a surface treatment configured to promote at least one of mechanical or chemical engagement between the inner surface and the thrombus and enable the thrombus to be pulled into lumen 22 of catheter 12 more effectively. For example, a coating may be applied to portions of the inner surface of expandable member 20 (e.g., the inner surface of the struts or braided filaments, or a flexible membrane 38 if present), where the coating has a relatively high clot affinity. Such affinity may be measured, for example, with a dynamic mechanical analyzer (DMA) equipped with a shear sandwich clamp. Examples of suitable coating materials to increase the affinity of the thrombus to expandable member 20 may include, for example, a thermoplastic elastomer such as ChronoPrene™ (AdvanSource Biomaterials, Wilmington, Massachusetts), ChronoPrene™ (AdvanSource Biomaterials, Wilmington, Massachusetts), ChronoPrene™ 5A, ChronoPrene™ 15A; a polyolefin elastomer such as ethylene-octene or ethylene-butene copolymer, for example, ENGAGE™ Polyolefin Elastomers (Dow Chemical Company, Midland, Michigan), ENGAGE™ 8107, 7367, 7270; or the like.

As another example, portions of the inner surface of expandable member 20 may be textured via etching or otherwise roughened (or rougher) in comparison to the outer surface of the expandable member 20 to better mechanically engage the thrombus. In some examples, an inner surface of expandable member 20 can include a polymer that is etched to promote mechanical thrombus engagement. In some examples, thrombus engagement with expandable member 20 may be enhanced by delivering electrical energy to expandable member 20.

Expandable member 20 may expand from a compressed (or "delivery") configuration to an expanded (or "deployed") configuration using any suitable technique. In some examples, expandable member 20 may be configured to self-expand. For example, the expandable frame of expandable member 20 may be formed from a metal and may include a shape-memory material such as Nitinol (and, optionally, additional material(s) or metal(s) such as radiopaque material(s) or metal(s)). In some such examples, and as described further below, flexible cover 44 of delivery-assist tool 14 can be positioned over expandable member 20 to facilitate retention of expandable member 20 in a collapsed configuration within delivery sheath 34, e.g., during navigation of elongated body 16 through delivery sheath 34 to a target treatment site within the vasculature of a patient. Once at the target treatment site, delivery sheath 34 can be retracted or elongated body 16 may be extended distally outward from sheath 34, and flexible cover 44 may be inverted and withdrawn through inner lumen 22 to allow expandable member 20 to expand radially outward to the deployed configuration.

In other examples, an electrical energy may be used to expand expandable member 20. For example, expandable member 20 (or a portion or a layer thereof) may be formed from a material or metal that bends or deflects in response to a current passed therethrough (or to heat generated as a result of such current). One such type of material is shape memory alloy actuator material, e.g., nitinol or Flexinol™ available from Dynalloy, Inc. of Irvine, California USA.

Hub 18 may be positioned at (e.g., proximal to or at least partially overlapping with) a proximal body portion 16A of elongated body 16. Proximal end 18A of hub 18 may define the catheter proximal end 12A of catheter 12 and may include a proximal opening 40 aligned with inner lumen 22B of elongated body 16, such that inner lumen 22B of elongated body 16 may be accessed via opening 40 and, in some examples, closed via opening 40. For example, hub 18 may include a luer connector, a hemostasis valve, or another mechanism or combination of mechanisms for connecting hub 18 to another device such as a vacuum source for performing the aspiration techniques described herein. In some examples, proximal end 12A of catheter 12 can include another structure in addition to, or instead of, hub 18.

In some examples, one or more portions of the inner surface of inner liner 24 defining inner lumen 22B (and in some examples, the inner surface of expandable member 20 defining inner lumen 22C) may be lubricious to facilitate the introduction and passage of a medical device (e.g., delivery-assist tool 14, another catheter, a guide member, an embolic protection device, a stent, a thrombectomy device, or any combination thereof), a therapeutic agent, a thrombus, or the like, through lumen 22B. A lubricious inner liner 24 may also enable relatively easy tracking of elongated body 16 over a guide member (e.g., a guidewire or a microcatheter). In some examples, the material from which portions of inner liner 24 is formed may itself be lubricious (e.g., PTFE). In addition to, or instead of, being formed from a lubricious material, in some examples, an inner surface of inner liner 24 is coated with a lubricious coating such as a hydrophilic coating.

Elongated body 16 includes one or more structural support members 28 positioned over inner liner 24. Structural support member 28 is configured to increase the structural integrity of elongated body 16 while allowing elongated body 16 to remain relatively flexible. For example, structural support member 28 may be configured to help elongated body 16 substantially maintain its cross-sectional shape (e.g., circular, or nearly circular) or at least help prevent elongated body 16 from buckling or kinking as it is navigated through tortuous anatomy. Additionally, or alternatively, structural support member 28, together with inner liner 24, and outer jacket 26, may help distribute both pushing and rotational forces along a length of elongated body 16, which may help prevent kinking of elongated body 16 upon rotation of body 16 or help prevent buckling of body 16 upon application of a pushing force to body 16. As a result, a clinician may apply pushing forces, rotational forces, or both, to the proximal portion of elongated body 16, and such forces may cause a distal portion of elongated body 16 to advance distally, rotate, or both, respectively.

Structural support member 28 may include one or more tubular braided structures, one or more coil members defining a plurality of turns, e.g., in the shape of a helix, or a combination of one or more braided structures and one or more coil members. Thus, although the examples of the disclosure primarily describe structural support member 28 as a coil, in other examples, catheter 12 may include a braided structure instead of a coil, a braided structure in addition to a coil, or a combination that includes one or more of each structure. As one example, a proximal portion of structural support member 28 may include a braided structure and a distal portion of structural support member 28 may include a coil member.

Structural support member 28 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 28 may include one or more metal wires braided or coiled around inner liner 24. The metal wires may include round wires, flat-round wires, flat wires, or any combination thereof.

Elongated body 16 can also include outer jacket 26 positioned over structural support member 28 and inner liner 24, the structural support member 28 being positioned between portions of inner liner 24 and outer jacket 26. In some examples, outer jacket 26 may be formed to have a stiffness that decreases from a proximal end of elongated body 16 toward expandable member 20. The lowered stiffness of outer jacket 26 within the distal body portion 16B of elongated body 16 may improve the flexibility and navigability of catheter 12 through tortious vasculature of the patient, while the relatively higher stiffness of outer jacket 26 within the proximal body portion 16A of catheter 12 may provide better pushability or kink resistance. In some examples, outer jacket 26 may be formed from two or more different materials with different mechanical properties that enable outer jacket 26 to exhibit the desired stiffness characteristics. In some examples outer jacket 26 may define a stiffness that is greater than the stiffness of flexible membrane 38 of expandable member 20.

In some examples, at least a portion of an outer surface of outer jacket 26 and/or expandable member 20 includes one or more coatings, such as, but not limited to, an anti-thrombogenic coating, which may help reduce the formation of thrombi in vitro, an anti-microbial coating, and/or a lubricating coating. The lubricating coating can be, for example, a hydrophilic coating.

Medical assembly 10 further includes a delivery-assist tool 14 configured to facilitate delivery of catheter 12 through delivery sheath 34. As illustrated in FIGS. 1A and 1B, delivery-assist tool 14 includes a flexible cover 44 configured to receive expandable member 20 and cause expandable member 20 to collapse or neck down into its delivery configuration (and/or retain expandable member 20 in its delivery configuration) for improved delivery through delivery sheath 34.

For instance, flexible cover 44 is configured to receive and constrain expandable member 20 in order to reduce the pushing force required to advance the catheter 12 through an inner lumen 58 of delivery sheath 34, as compared to examples in which expandable member 20 is directly introduced into, and advanced through, delivery sheath 34 without the aid of such a delivery-assist tool. For example, as flexible cover 44 is introduced into lumen 58 of delivery sheath 34, flexible cover 44 may begin to neck down in response to contact with the interior surface of delivery sheath 34 and may thereby cause the received expandable member 20 to elongate and neck down as well. As a result, flexible cover 44 may redirect the applied force from delivery sheath 34 to exert a tensile pulling force on expandable member 20, which may reduce or minimize the force of delivery (e.g., by avoiding the bunching and compression of expandable member 20 that may otherwise result from a compressive pushing force caused by direct friction between expandable member 20 and the sheath 34).

FIGS. 1A, 1B, and 2 depict a first example of delivery-assist tool 14. In the example depicted in FIGS. 1A, 1B, and 2, delivery-assist tool 14 includes an elongated support structure 42 and a flexible cover 44 located at or near a distal portion 42B of support structure 42.

Elongated support structure 42 includes an elongated body configured to support and enable delivery of flexible cover 44 distally through inner lumen 22 of catheter 12 for subsequent positioning of flexible cover 44 over expandable member 20. A clinician may also grasp elongated support structure 42 to proximally withdraw flexible cover 44 back through inner lumen 22. Elongated support structure 42 may include a guidewire, a rod, a hypotube or other hollow tubing, or another similar structure sized to fit through inner lumen 22 of catheter 12. For instance, support structure 42 may include polymer tubing, such as, but not limited to, high-density polyethylene (HDPE) tubing. Support structure 42 may be rigid enough to deliver flexible cover 44 distally through inner lumen 22 of catheter 12 in response to a distal force applied, e.g., to proximal portion 42A. Support structure 42 may further be flexible enough to navigate through tortuous vasculature of the patient while positioned inside inner lumen 22 of catheter 12.

In some examples, support structure 42 defines a variable durometer along its length. For instance, support structure 42 may define a stiffer or more-rigid proximal portion 42A to better support delivery of flexible cover 44 through lumen 22 of catheter 12. Additionally, or alternatively, support structure 42 may define a less-rigid distal portion 42B. For instance, distal portion 42B may define a flexible, atraumatic distal tip of delivery-assist tool 14 that extends distally to flexible cover 44, e.g., to reduce adverse interactions with a vessel wall of the patient.

Delivery-assist tool 14 has an axial length that exceeds the axial length (measured along a longitudinal axis of support structure 42) of catheter 12, such that distal portion 42B of support structure 42 and flexible cover 44 are capable of extending distally outward from catheter distal mouth 32 while support structure proximal portion 42A at least partially extends proximally outward from catheter proximal mouth 40.

As illustrated in FIG. 2, flexible cover 44 is located at or near a distal portion 42B of support structure 42. For instance, flexible cover 44 may be located at a distal-most end of support structure 42 or may be positioned just proximal to the distal-most end, such as in examples in which support structure 42 includes an atraumatic distal tip. In such examples, support structure 42 extends distally through flexible cover 44.

Proximal end 44A of flexible cover 44 defines a proximal-facing mouth 56 that opens into an interior cavity 46 configured to receive at least a distal portion of expandable member 20. Flexible cover 44 helps facilitate introduction of expandable member 20 into inner lumen 58 of delivery sheath 34 and facilitates distal advancement of expandable member 20 through the inner lumen 58 of delivery sheath 34. In some examples, flexible cover 44 includes a relatively thin, flexible substrate formed into a tubular or funnel shape, e.g., a sleeve that tapers in a distal direction from proximal mouth 56 to distal end 44B. In some examples, flexible cover 44 may be formed from polyethylene terephthalate (PET) or another polymer. In some examples, flexible cover 44 may include a closed, continuous surface, e.g., formed from a single unit of material. In other examples, flexible cover 44 may include a braid, weave, or other mesh structure formed from a plurality of filaments and/or defining a plurality of pores or gaps.

An interior surface of flexible cover 44 is configured to contact an exterior surface of expandable member 20 and apply a compressive force that causes expandable member 20 to contract radially inward to the delivery configuration to facilitate distal advancement through an inner lumen 58 of delivery sheath 34. For example, the interior surface of flexible cover 44 may transmit to expandable member 20 a compressive force applied to flexible cover 44 by an inner surface of delivery sheath 34 (the inner surface defining the inner lumen 58 of delivery sheath 34). Accordingly, the materials and structure for both expandable member 20 and flexible cover 44 are configured such that an applied force between expandable member 20 and flexible cover 44 causes expandable member 20 to deform (e.g., contract radially inward) rather than causing flexible cover 44 to deform (e.g., expand radially outward).

In some examples, flexible cover 44 is configured to be less flexible or more rigid, particularly in a radial and/or circumferential direction, than expandable member 20, in order to keep expandable member 20 restrained radially inward in the delivery configuration for delivery through delivery sheath 34. For instance, in some examples, both expandable member 20 and flexible cover 44 may be formed from braided filaments, such as Nitinol wires or the like. Either or both of the braided structures of expandable member 20 and flexible cover 44 may be configured to radially expand and contract through a toy-finger-trap-type mechanism, in which the braided structure contracts radially inward as it elongates along a longitudinal direction (e.g., along central longitudinal axis 30). Accordingly, a higher radial stiffness of flexible cover 44 may be achieved via a higher axial extensibility (e.g., longitudinal stretchiness, or "rate of axial elongation") of the braided structure of flexible cover 44. The rates of axial elongation of the structures of expandable member 20 and flexible cover 44 may depend on several different factors, such as braid angle, braid density, filament count, or the like, which may be varied and selected to achieve the desired properties of expandable member 20 and flexible cover 44. For instance, the rate of axial elongation of the flexible cover 44 may be selected to be comparable to, or greater than, the rate of axial elongation of the flexible cover 44 in order for the delivery-assist tool 14 to function as described herein.

For instance, the filaments of flexible cover 44 may be braided so as to define a braid angle 47 that is larger than a braid angle of expandable member 20. A "braid angle" refers to the angle between a filament of the braided structure and the longitudinal axis of the braided structure. A higher braid angle 47 of the filaments of flexible cover 44 may contribute to a higher rate of axial elongation as the cross-sectional profile of the flexible cover 44 is constrained, e.g., when compressed radially inward for delivery through sheath 34. As described above, the higher rate of axial elongation of the flexible cover 44 may correspond to a stronger tensile force imparted from the flexible cover 44 radially inward onto the expandable member 20 to keep the expandable member 20 constrained in the delivery configuration for delivery through the sheath 34. In this way, a higher rate of axial elongation of the flexible cover 44 (as compared to the corresponding rate of axial elongation of the expandable member 20) may better aid in delivery of system 10 through delivery sheath 34. As one illustrative example, filaments of expandable member 20 may have a braid angle of about 60 degrees to about 70 degrees, while filaments of flexible cover 44 may have a braid angle 47 of about 70 degrees to about 80 degrees.

Additionally or alternatively, the filaments of flexible cover 44 may be braided more closely than the filaments of expandable member 20, such that flexible cover 44 defines a mesh density that is higher than a mesh density of expandable member 20. As one illustrative example, expandable member 20 may have a mesh density of about 60 picks per inch (PPI), while flexible cover 44 may have a mesh density from about 150 PPI to about 200 PPI. Additionally, or alternatively, the filaments of flexible cover 44 may include thicker-diameter wires than the filaments of expandable member 20. Additionally, or alternatively, the filaments of flexible cover 44 may be formed from a more-rigid material (e.g., chemical composition) than the filaments of expandable member 20.

As detailed further below, in some examples, flexible cover 44 is configured to be rigid enough to compress expandable member 20, but flexible enough to be easily removed from expandable member 20 by inverting in response to a proximal force, e.g., applied to proximal portion 42A of support structure 42.

In any of the examples described herein, distal portion 42B of support structure 42 may be coterminous with a distal-most end of flexible cover 44 (or equivalent structure, as described further below). In other words, in some examples, support structure 42 may not extend distally past a point at which flexible cover 44 attaches to support structure 42. In other examples in which support structure 42 does include a distal portion 42B that extends distally past flexible cover 44, distal portion 42B may include a substantially flexible material, defining an atraumatic distal tip of delivery-assist tool 14.

FIG. 3 is side view of a distal portion of a delivery-assist tool 48, which may be another example of delivery-assist tool 14 of medical assembly 10 of FIGS. 1A and 1B. Similar to delivery-assist tool 14, delivery-assist tool 48 includes an elongated support structure 50, which may be an example of elongated support structure 42. However, unlike delivery-assist tool 14, which flexible cover 44 includes a tubular sleeve, flexible cover 52 of delivery-assist tool 48 includes an end cap defining a plurality of extensions or flaps 54 configured to engage with an outer surface of expandable member 20. For instance, flaps 54 may include elongated prongs or "petals" that extend both radially outward and proximally, e.g., from a distal portion 50B of elongated support structure 50 toward a proximal portion 50A. In some examples, flexible cover 52, including flaps 54, may be formed (e.g., cut) from a single unit of material, such as a polymer or from a nickel-titanium alloy (i.e., Nitinol). In other examples, flaps 54 may be physically separate from each other and coupled to support structure 50 or to another structure to define flexible cover 52. The example delivery-assist tool 48 depicted in FIG. 3 includes three flaps 54, however, tool 48 may include any number of flaps, such as two to six flaps or more.

Flaps 54 are configured to transmit a compressive force to expandable member 20 of catheter 12 to facilitate introduction of expandable member 20 into delivery sheath 34 and facilitate distal advancement of expandable member 20 through delivery sheath 34. For example, similar to flexible cover 44 (FIG. 2), flaps 54 may collectively define an interior volume configured to receive all or part of expandable member 20. When support structure 50 extends through inner lumen 22 of catheter 12 and expandable member 20 is in the interior volume defined by flaps 54 (that is, when flaps 54 are positioned over expandable member), delivery-assist tool 48 and catheter 12 may be introduced into the inner lumen 58 of delivery sheath 34. Flaps 54 are configured to transmit a compressive force applied by the inner surface of delivery sheath 34 to cause expandable member 20 to assume a delivery configuration. For example, flaps 54 may apply an axial tensile force to expandable member 20 to cause expandable member to neck down (e.g., elongate and compress radially inward).

Similar to flexible cover 44 of FIGS. 1A-2, flexible cover 52 of FIG. 3 may be configured to invert to release expandable member 20. For instance, in response to a proximal pulling force applied to elongated support structure 50, a resulting contact with distal end 20B of expandable member 20 may cause the free ends 54A of flaps 54 (e.g., the ends that are not coupled to one another via a portion of flexible cover 52 that does not define flaps 54) to move distally into a position that is distal to fixed ends 54B. In this inverted configuration, delivery-assist tool 48 may then be proximally withdrawn through inner lumen 22 of catheter 12.

In other examples (not shown), instead of flexible cover 52, delivery-assist tool 48 may include a spiral or helical structure extending circumferentially around support structure 50, radially outward from distal portion 50B of support structure 50, and proximally, e.g., from a distal portion 50B of elongated support structure 50 toward a proximal portion 50A. The helical structure may or may not include a flexible membrane defining an internal cavity within the helical structure.

Figure 4:
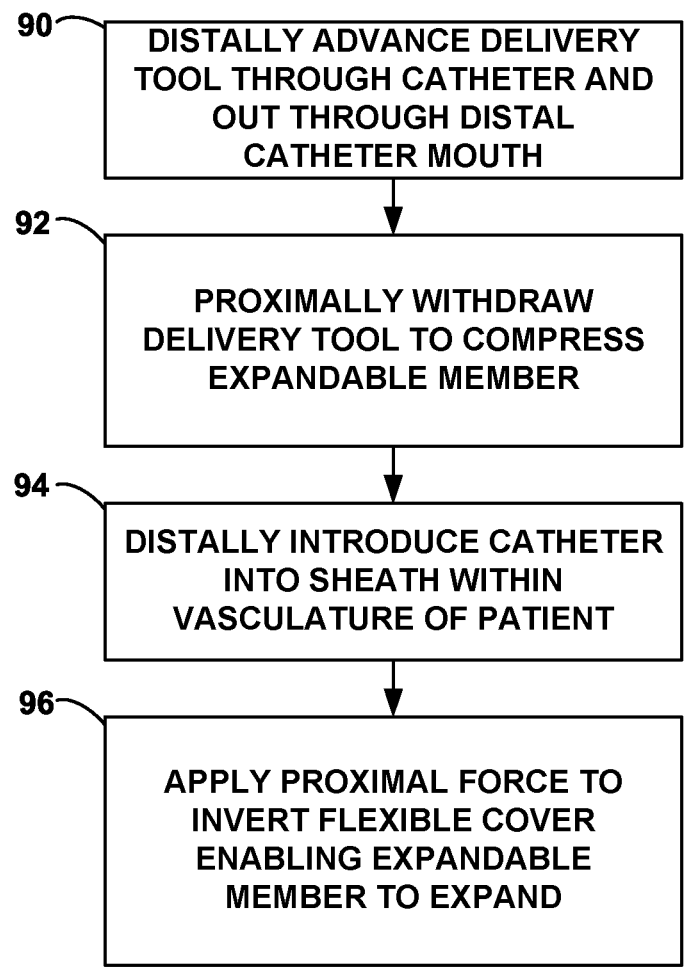
FIG. 4 flow diagram of an example method of using a medical assembly.
Figure 5A:
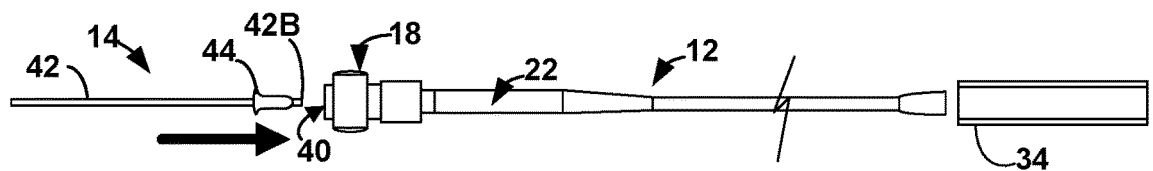
FIGS. 5A-5J are conceptual diagrams illustrating the method of FIG. 4.
Figure 5B:
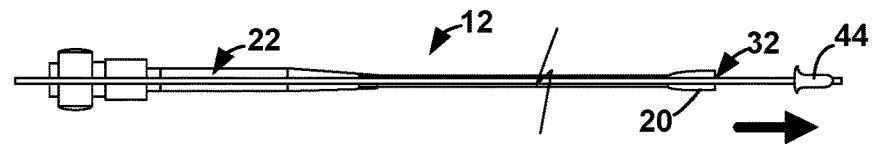
Figure 5C:
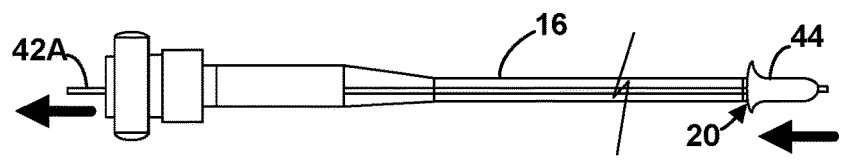
Figure 5D:
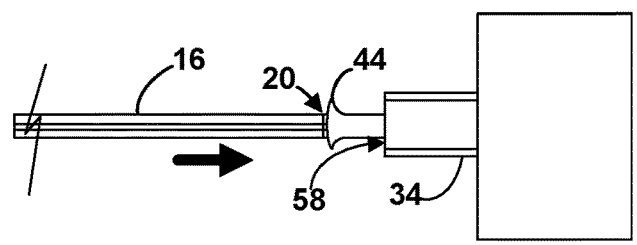
Figure 5E:
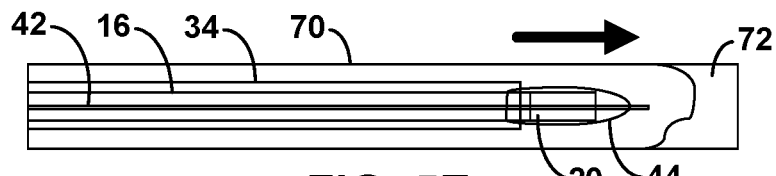

FIG. 4 is a flow diagram of an example method of aspiration using medical assembly 10 of FIGS. 1A and 1B. The techniques of FIG. 4 are described herein with respect to the conceptual diagrams of FIGS. 5A-5J illustrating the method. While FIGS. 4-5J are primarily described with reference to delivery-assist tool 14, in other examples, the technique may also be used with delivery-assist tool 48 of FIG. 3 or other delivery-assist tools including a flexible cover in accordance with examples described herein.

The method includes distally advancing delivery-assist tool 14 through inner lumen 22 of catheter 12 and out through distal mouth 32 of catheter 12 (90). For instance, as shown in FIG. 5A, a clinician may introduce a distal portion 42B of delivery tool 14 into proximal mouth 40 of catheter 12, and advance delivery-assist tool 14 through inner lumen 22 of catheter 12. As shown in FIG. 5B, the clinician may distally advance delivery-assist tool 14 into until flexible cover 44 of delivery-assist tool 14 extends entirely outward from distal mouth 32 of expandable member 20.

In some examples, the method further includes proximally withdrawing delivery-assist tool 14 to cover expandable member 20 with flexible cover 44 (92). For instance, as shown in FIG. 5C, once flexible cover 44 of delivery-assist tool 14 extends entirely outward from distal mouth 32, the clinician may apply a proximal force or pressure, e.g., to proximal portion 42A of support structure 42, to at least partially withdraw support structure 42 back into inner lumen 22. In this way, flexible cover 44 receives expandable member 20 within inner cavity 46. Alternatively, or in addition to pushing tool 14 proximally, the clinician may push catheter 12 distally to position expandable member 20 in cavity 46 of flexible cover 44 of tool 14.

In some examples, the inner surface of flexible cover 44 may apply a compressive force to compress expandable member 20 into the delivery configuration. In other examples, however, flexible cover 44 may not begin to apply a compressive force to expandable member 20 until a compressive force is applied to flexible cover 44, such as by an inner surface of delivery sheath 34.

In some examples, but not all examples, after flexible cover 44 is positioned over expandable member 20, the clinician may then engage (e.g., tighten) a locking mechanism to fix flexible cover 44 in place over top of expandable member 20. In some such examples, tightening the locking mechanism fixes the proximal portion of support structure 42 in place with respect to the catheter 12, e.g., to prevent any relative longitudinal "slipping" (movement) of the delivery-assist tool 14. This further allows the delivery-assist tool 14 and the catheter 12 to longitudinally move as effectively one structure in response to a pushing force applied to either the catheter 12 or the delivery-assist tool 14. In some examples, the locking mechanism may include a rotating hemostasis valve (RHV). In other examples, the locking mechanism may include a slider or switch that is integrated into the hub 18 of the catheter 12 which, when actuated, clamps down on the support structure 42 of the delivery-assist tool 14.

In some examples in which the locking mechanism is not engaged, pushing on the delivery-assist tool 14 or the catheter 12 may result in some amount of longitudinal movement between the two components. In some such examples, the tensile force imparted by the flexible cover 44 onto the expandable member 20 when the delivery-assist tool 14 is pushed may be enough to keep the expandable member 20 constrained during sheath delivery, but not enough to pull the entire catheter 12 (including the proximal body portion 16A) through the sheath 34, and the flexible cover 44 can begin slipping off of the expandable member 20. For the entire system 10 to deliver smoothly through the sheath 34, it may be advantageous to have both a pulling force (e.g., from the necked-down flexible cover 44) on the distal end of the catheter 12, and a pushing force from the proximal end of the catheter 12, which is longitudinally fixed relative to the support structure 42.

The method further includes introducing catheter 12 and delivery-assist tool 14 into delivery sheath 34 (94). For instance, as shown in FIG. 5D-5F, a distal portion of catheter 12, including expandable member 20 and flexible cover 44, may be introduced into a proximal opening of introducer sheath 34, which has been inserted within vasculature 70 of a patient and defines a passageway toward a target treatment site within the patient, such as toward a thrombus 72 within the patient's vasculature.

An inner surface of delivery sheath 34 applies a radially inward force on flexible cover 44 which causes flexible cover 44 to neck down into a smaller outer cross-sectional dimension and, in some cases, elongate. As flexible cover 44 compresses, expandable member 20 within cavity 46 of flexible cover 44 also compresses. In some examples, as flexible cover 44 necks down onto expandable member 20, flexible cover 44 exerts an axial tensile pulling force (e.g., in a longitudinal or axial direction) onto expandable member 20 rather than only a radially compressive force, similar to the mechanism of a toy finger trap. In this way, delivery-assist tool 14 significantly reduces a "bunching" of the material of expandable member 20 that would otherwise result from contact with an interior surface of introducer sheath 34. This type of undesired bunching would typically increase a frictional force between the expandable member 20 and an interior surface of sheath 34, thereby making insertion of catheter 12 through sheath 34 more difficult (e.g., by increasing the insertion force required to overcome the frictional force).

Instead, in this delivery configuration, an outer diameter of expandable member 20 is compressed to be smaller than an inner diameter of delivery sheath 34, reducing an amount of friction between expandable member 20 and an inner surface of delivery sheath 34, and thereby reducing an amount of force required to advance catheter 12 through delivery sheath 34.

Figure 5F:
Figure 5G:
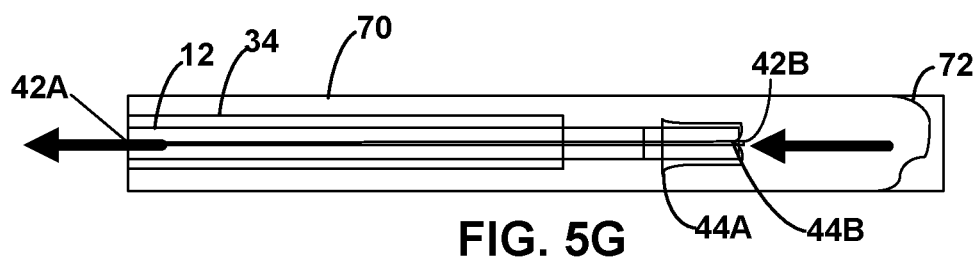
Figure 5H:
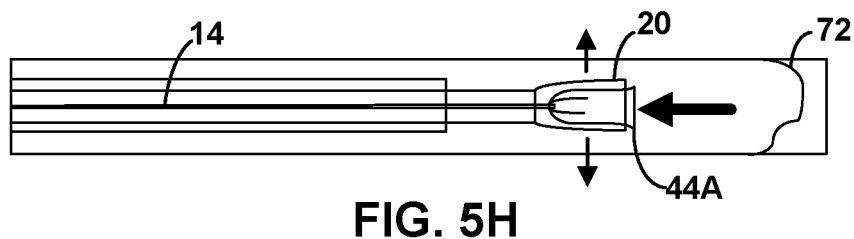
Figure 5I:
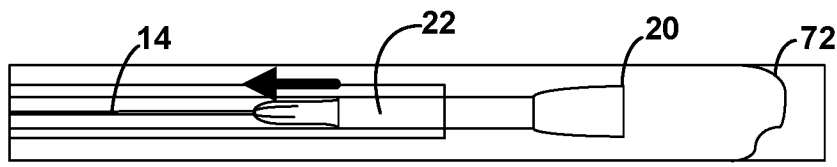
Figure 5J:
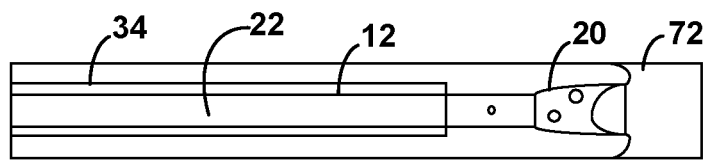

As shown in FIG. 5F, catheter 12 may be advanced through an inner lumen 58 of the introducer sheath until expandable member 20 and/or flexible cover 44 extend distally outward from a distal mouth 34B of introducer sheath 34. In some examples, the method further includes applying a proximal force to delivery-assist tool 14 to invert flexible cover 44, thereby enabling expandable member 20 to expand (96). For instance, as shown in FIG. 5G, the clinician may apply a proximal force, e.g., to proximal portion 42A of support structure 42, to proximally withdraw distal end 42B of support structure 42 into lumen 22 of catheter 12. As distal portion 42B of support structure 42 proximally withdraws distal portion 44B of flexible covering 44 (to which support structure 42 is rigidly coupled), a drag force between an exterior surface of expandable member 20 and an interior surface of flexible covering 44 causes flexible covering 44 to invert and evert, as shown in FIG. 5H. With flexible covering 44 inverted and no longer compressing expandable member 20 radially inward, expandable member is able to self-expand (or expand manually via any incorporated mechanism) radially outward into the expanded or deployed configuration. As shown in FIG. 5I, the clinician may proximally withdraw delivery-assist tool 14 through lumen 22 of catheter 12 and out from the patient's body.

In some examples, as shown in FIG. 5J, the clinician may actuate an aspiration force within inner lumen 22 of catheter 12, such that portions of thrombus 72 are aspirated into expandable member 20 and proximally through lumen 22. Catheter 12 may be removed from the vasculature once the aspiration procedure is complete.

Various aspects of the disclosure have been described. These and other aspects are within the scope of the following claims.

What is claimed is:

1. A medical assembly comprising:
   a catheter comprising:
      an elongated body comprising a proximal body portion and a distal body portion and defining a body inner lumen, wherein the proximal body portion defines a proximal opening to the body inner lumen and the distal body portion defines a distal opening to the body inner lumen; and
      an expandable member located at the distal body portion, the expandable member defining an expandable member inner lumen, wherein the expandable member is configured to expand radially outward from a delivery configuration to a deployed configuration, and wherein the expandable member inner lumen is in fluid communication with the body inner lumen; and
   a delivery-assist tool comprising:
      a support structure configured to extend through the body inner lumen and the expandable member inner lumen; and a flexible cover coupled to a distal portion of the support structure, wherein the flexible cover is configured to facilitate compression and retention of the expandable member in the delivery configuration while the catheter is being advanced through a delivery sheath and while the support structure extends through the body inner lumen and the expandable member inner lumen, and wherein the flexible cover is configured to invert and proximally withdraw through the body inner lumen in response to a proximal force applied to the support structure.

2. The assembly of claim 1, wherein the flexible cover has a funnel shape defining a proximal-facing mouth when the flexible cover is disposed over the expandable member and is compressing the expandable member.

3. The assembly of claim 1, wherein the flexible cover is configured to extend distally past a distal-most end of the expandable member, and further configured to apply an axial tensile force to the expandable member while the flexible cover is disposed over the expandable member and while the flexible cover and the expandable member are disposed within the delivery sheath.

4. The assembly of claim 1, wherein the flexible cover comprises a braided mesh.

5. The assembly of claim 4, wherein the braided mesh comprises Nitinol.

6. The assembly of claim 4, wherein the braided mesh comprises polyethylene terephthalate (PET).

7. The assembly of claim 4, wherein the braided mesh defines a first braid angle that is greater than a second braid angle of the expandable member.

8. The assembly of claim 1, wherein the flexible cover comprises a plurality of polymer flaps extending proximally and radially outward from the support structure.

9. The assembly of claim 1, wherein the flexible cover comprises a plurality of Nitinol petals extending proximally and radially outward from the support structure.

10. The assembly of claim 1, wherein the flexible cover comprises a coil structure extending helically around the support structure.

11. The assembly of claim 1, wherein the support structure comprises polymer.

12. The assembly of claim 1, wherein the support structure defines a varying hardness along an axial length of the support structure.

13. The assembly of claim 12, wherein the support structure defines a proximal portion and the distal portion, wherein the distal portion defines a hardness that is less than a hardness of the proximal portion.

14. The assembly of claim 1, further comprising the delivery sheath.

15. The assembly of claim 1, wherein the catheter further comprises a locking mechanism configured to engage with the support structure of the delivery-assist tool to minimize or prevent longitudinal movement of the delivery-assist tool relative to the catheter.

16. The assembly of claim 15, wherein the locking mechanism comprises a hemostasis valve.

17. A catheter comprising:
an elongated body including a proximal body portion and a distal body portion and defining a body inner lumen, wherein the proximal body portion defines a proximal opening to the body inner lumen and the distal body portion defines a distal opening to the body inner lumen;
an expandable member located at the distal body portion, the expandable member forming an expandable member inner lumen, the expandable member inner lumen defining a distal extension of the body inner lumen in fluid communication with the body inner lumen, wherein the expandable member is configured to expand radially outward from a delivery configuration to a deployed configuration; and
a delivery-assist tool configured to be received within the body inner lumen and the expandable member inner lumen, the delivery-assist tool comprising a support structure and a mesh cover configured to apply an axial tensile force to the expandable member to facilitate compression of the expandable member into the delivery configuration as the expandable member and the mesh cover are advanced through a delivery sheath, wherein the mesh cover is configured to invert and proximally withdraw through the body inner lumen in response to a proximal force applied to the support structure.

18. The catheter of claim 17, wherein the mesh cover defines a first braid angle that is greater than a second braid angle of the expandable member.

19. A method comprising:
introducing a delivery-assist tool comprising a support structure and a flexible cover coupled to a distal portion of the support structure into a body inner lumen of a catheter, wherein the elongated body comprises a proximal body portion and a distal body portion, wherein the proximal body portion defines a proximal opening to the body inner lumen and the distal body portion defines a distal opening to the body inner lumen, wherein introducing the delivery-assist tool comprises advancing the support structure and the flexible cover through the body inner lumen and positioning the flexible cover distal to an expandable member of the catheter, the expandable member defining an expandable member inner lumen in fluid communication with the body inner lumen, and wherein the expandable member is located at the distal body portion of the catheter;
while the support structure is positioned within and extends through the body inner lumen and the expandable member lumen, positioning the flexible cover over the expandable member;
distally introducing the catheter and the delivery-assist tool into a delivery sheath, wherein the flexible cover is configured to facilitate compression and retention of the expandable member into a delivery configuration while the catheter is being advanced through the delivery sheath and while the support structure extends through the body inner lumen and the expandable member inner lumen; and
applying a proximal force to the support structure to invert the flexible cover and proximally withdraw the flexible cover into the body inner lumen of the catheter, enabling the expandable member to expand radially outward from the delivery configuration to a deployed configuration.

20. The method of claim 19, wherein the flexible cover has a funnel shape defining a proximal-facing mouth when the flexible cover is disposed over the expandable member.

21. The method of claim 19, wherein the flexible cover is configured to neck down the expandable member by at least applying an axial tensile force to the expandable member while the flexible cover is disposed over the expandable member and while the flexible cover and the expandable member are disposed within the delivery sheath.

22. The method of claim 19, wherein the flexible cover comprises a braided mesh.

23. The method of claim 22, wherein the braided mesh defines a first braid angle that is greater than a second braid angle of the expandable member.

24. The method of claim 19, wherein the flexible cover comprises a plurality of polymer flaps extending proximally and radially outward from the support structure.

25. The method of claim 19, wherein the support structure defines a varying hardness along an axial length of the support structure.

\* \* \* \* \*